United States Patent
Hayashi et al.

(10) Patent No.: US 11,448,563 B2
(45) Date of Patent: Sep. 20, 2022

(54) FORCE MEASUREMENT METHOD, FORCE MEASUREMENT DEVICE, FORCE MEASUREMENT SYSTEM, FORCE MEASUREMENT PROGRAM, AND RECORDING MEDIUM

(71) Applicant: Tohoku University, Sendai (JP)

(72) Inventors: Kumiko Hayashi, Sendai (JP); Yasushi Okada, Wako (JP)

(73) Assignee: Tohoku University, Sendai (JP)

(*) Notice: Subject to any disclaimer, the term of this patent is extended or adjusted under 35 U.S.C. 154(b) by 337 days.

(21) Appl. No.: 16/759,040

(22) PCT Filed: Oct. 30, 2018

(86) PCT No.: PCT/JP2018/040300
§ 371 (c)(1),
(2) Date: Apr. 24, 2020

(87) PCT Pub. No.: WO2019/088089
PCT Pub. Date: May 9, 2019

(65) Prior Publication Data
US 2020/0333202 A1    Oct. 22, 2020

(30) Foreign Application Priority Data
Oct. 31, 2017 (JP) .............................. JP2017-210698

(51) Int. Cl.
*G01L 5/105*       (2020.01)
*G06F 17/18*       (2006.01)
*G01N 33/483*      (2006.01)

(52) U.S. Cl.
CPC .............. *G01L 5/105* (2013.01); *G06F 17/18* (2013.01); *G01N 33/483* (2013.01)

(58) Field of Classification Search
CPC .. G06F 17/18; C12M 1/34; G01L 1/00; G01L 5/105; G01N 21/85; G01N 33/483; C12Q 1/02
(Continued)

(56) References Cited

U.S. PATENT DOCUMENTS
2014/0067342 A1    3/2014  Calderon

FOREIGN PATENT DOCUMENTS
JP    H01-012187 Y2    4/1989
JP    2869422 B2        3/1999
(Continued)

OTHER PUBLICATIONS

International Search Report in connection with International Application No. PCT/JP2018/040300 dated Nov. 27, 2018.
(Continued)

*Primary Examiner* — John H Le
(74) *Attorney, Agent, or Firm* — Wolf, Greenfield & Sacks, P.C.

(57) ABSTRACT

One aspect of the present invention is a force measurement method including a first acquisition step in which, among data included in time course data indicating a movement trajectory of cargo acquired in a non-invasive manner, first data indicating a temporal change of a position of the cargo during a period in which the displacement of the cargo per unit time is substantially constant is acquired, a fluctuation value calculation step in which, based on a first probability distribution indicating a distribution of a probability that the amount of change at a predetermined position of the cargo per unit time is a predetermined amount, which is a probability distribution based on the first data, a fluctuation value proportional to a force applied to the cargo by motor proteins
(Continued)

that transport the cargo is calculated, and a force calculation step in which the force is calculated based on the calculated fluctuation value.

9 Claims, 13 Drawing Sheets

(58) Field of Classification Search
USPC .......................................................... 702/41
See application file for complete search history.

(56) References Cited

FOREIGN PATENT DOCUMENTS

| JP | 3195935 B2 | 8/2001 |
|---|---|---|
| JP | 2009-077635 A | 4/2009 |
| JP | 5569892 B2 | 8/2014 |
| JP | 2019-165694 A | 10/2019 |

OTHER PUBLICATIONS

Hayashi et al., Viscosity and drag force involved in organelle transport: Investigation of the fluctuation dissipation theorem. The European Physical Journal E. 2013;36:136. 7 pages. doi: 10.1140/epje/i2013-13136-6.
Japanese Notice of Allowance dated Apr. 27, 2021 in connection with Japanese Application No. 2017-210698.

———  REGRESSION LINE WITH RESPECT TO
        CONSTANT SPEED MOVEMENT DATA

+END DIRECTION TRANSPORT (CELL CENTER->CELL MEMBRANE)

-END DIRECTION TRANSPORT (CELL CENTER->CELL MEMBRANE)

FORCE MEASUREMENT METHOD, FORCE MEASUREMENT DEVICE, FORCE MEASUREMENT SYSTEM, FORCE MEASUREMENT PROGRAM, AND RECORDING MEDIUM

CROSS-REFERENCE TO RELATED APPLICATIONS

This application is a 35 U.S.C. § 371 National Phase filing of International Application No. PCT/JP2018/040300, filed on Oct. 30, 2018, entitled "FORCE MEASUREMENT METHOD, FORCE MEASUREMENT DEVICE, FORCE MEASUREMENT SYSTEM, FORCE MEASUREMENT PROGRAM, AND RECORDING MEDIUM," which claims priority to and the benefit of Japanese Patent Application No. 2017-210698, filed on Oct. 31, 2017. The entire contents of these applications are incorporated herein by reference in their entirety.

TECHNICAL FIELD

The present invention relates to a force measurement method, a force measurement device, a force measurement system, a force measurement program, and a recording medium.

Priority is claimed on Japanese Patent Application No. 2017-210698, filed Oct. 31, 2017, the content of which is incorporated herein by reference.

BACKGROUND ART

Many eukaryotic cells have a developed intracellular transport system. In the related art, neurons have been used as a research subject for intracellular transport systems. Neurons have cell bodies and long extensions (axons) that extend from the cell body. The shape of a neuron is formed by a protein group constituting a cytoskeleton, and axons are mainly formed by tubulin constituting microtubules. Microtubules function as main lines of a logistics system (axonal transport) between the cell body and the synapse at the tip of the axon. Regarding examples of the cargo carried by axonal transport, intracellular organelles and vesicles covered by a lipid bilayer are known. Regarding examples of organelles, for example, mitochondria and endosomes are known. The vesicles contain substances that form axons and synapses, and proteins, nucleic acid polymers, and low-molecular-weight substances as information transmitting substances. Cargo transport includes anterograde transport from the cell body toward the tip of the axon and retrograde transport in a direction opposite thereto. In the anterograde transport, it is known that motor proteins called kinesin carry the cargo moving along microtubules. Similarly, in retrograde transport, motor proteins called dynein are responsible for transporting the cargo. Motor proteins transport the cargo using energy obtained by ATP hydrolysis.

Disfunction of axonal transport is thought to be one cause of neurological diseases such as Alzheimer's disease or Parkinson's disease, and analysis of axonal transport is expected to contribute to the understanding and treatment of neurological diseases.

While the cargo transport by motor proteins has been described above using axonal transport as a specific example, the transport of cargo by motor proteins is not limited to axonal transport. In neurons, the cargo is transported not only in the axon but also in extensions such as dendrites or in the cell body. In this case, the cargo is not necessarily covered with a lipid bilayer, but may be a protein complex or a protein-nucleic acid complex. In addition, regarding motor proteins, not only kinesin or dynein that move along microtubules, but also various motor molecules such as myosin that move on actin fibers may be used. In addition, intracellular transport is performed not only in neurons, but also in all eukaryotic cells according to the same mechanism. For example, in skin melanocytes, intracellular granules containing melanin are transported as cargo, and in insulin-secreting cells of the pancreas, intracellular vesicles containing insulin are transported as the cargo. That is, while the transport of cargo by motor proteins has been described above using neurons as a specific example, the transport of cargo by motor proteins is not necessarily performed only in neurons, and may also in cells other than neurons. For example, in cells other than neurons, the cargo transport by motor proteins is performed by motor proteins moving on microtubules in addition to the axon.

In the related art, in order to analyze such cargo transport, the force applied to cargo in living cells has been measured. A method of measuring a force applied to cargo in living cells is, for example, a method using optical tweezers. The method using optical tweezers is a method of applying a force to cargo to be observed using optical tweezers and measuring the force applied to the cargo by pulling the cargo. Here, the force applied to the cargo is, for example, a force applied to the cargo by motor proteins.

CITATION LIST

Patent Literature

[Patent Literature 1]
Japanese Unexamined Patent Application, First Publication No. 2009-77635

Non-Patent Literature

[Non-Patent Literature 1]
K. Hayashi, C. G. Pack, M. K. Sato, K. Mouri, K. Kaizu, K. Takahashi, and Y. Okada, "Viscosity and drag force involved in organelle transport: Investigation of the fluctuation dissipation theorem", The European Physical Journal E, 36:136 (2013)

SUMMARY OF INVENTION

Technical Problem

However, it is difficult to apply the method using optical tweezers other than to specific cargo such as oil droplets because a refractive index difference between the cargo and cytoplasm therearound, the size of the cargo, and an intensity of a laser beam determine a generated force. As a result, when the method using optical tweezers is applied to cargo other than oil droplets, a laser beam with an excessive intensity is necessary, and cell invasion and thermal damage may occur.

In this manner, since the method using optical tweezers is an invasive method using a laser beam, there is a problem that cells to be observed may be damaged.

In view of the above circumstances, an object of the present invention is to provide a technique for measuring a force applied to cargo in living cells in a non-invasive manner.

Solution to Problem

One aspect of the present invention is a force measurement method including a first acquisition step in which, among data included in time course data indicating a movement trajectory of cargo acquired in a non-invasive manner, first data indicating a temporal change of a position of the cargo during a period in which the displacement of the cargo per unit time is substantially constant is acquired, a fluctuation value calculation step in which, based on a first probability distribution indicating a distribution of a probability that the amount of change at a predetermined position of the cargo per unit time is a predetermined amount, which is a probability distribution based on the first data, a fluctuation value proportional to a force applied to the cargo by motor proteins that transport the cargo is calculated, and a force calculation step in which the force is calculated based on the calculated fluctuation value.

In another aspect of the present invention, in the force measurement method, in the force calculation step, the force is calculated by performing clustering on the fluctuation value.

In another aspect of the present invention, the force measurement method further includes a second acquisition step in which, among time course data indicating a movement trajectory of the cargo acquired in a non-invasive manner, time course data including the first data and second data indicating a temporal change of the position of the cargo during a period in which the position of the cargo is substantially the same position regardless of time is acquired; and a fluctuation coefficient calculation step in which a fluctuation coefficient which is a conversion coefficient with respect to between the force and the fluctuation value is calculated based on the first and second data.

In another aspect of the present invention, in accordance with the force measurement method, in the fluctuation coefficient calculation step, a viscosity coefficient of a medium surrounding the cargo is calculated based on the second data.

In another aspect of the present invention, in accordance with the force measurement method, in the fluctuation coefficient calculation step, a speed at which the cargo moves is calculated based on the first data acquired in the second acquisition step.

In another aspect of the present invention, in accordance with the force measurement method, in the fluctuation coefficient calculation step, the fluctuation coefficient is calculated based on the viscosity coefficient and the speed.

In another aspect of the present invention, in accordance with the force measurement method, in the fluctuation value calculation step, $\chi$ is calculated according to a formula of $\chi = \ln[P1(\Delta X_1)/P1(-\Delta X_1)]\Delta X_1$ when the amount of change in the position is set as $\Delta X$, a probability that the value of $\Delta X$ during the unit time is $\Delta X_1$ is set as a first probability $P1(\Delta X_1)$, and the fluctuation value is set as $\chi$.

Another aspect of the present invention is a force measurement device, including: a first acquisition unit configured to acquire first data indicating a temporal change of a position of cargo during a period in which the displacement of the cargo per unit time is substantially constant among data included in time course data indicating a movement trajectory of the cargo acquired in a non-invasive manner, a fluctuation value calculation unit configured to calculate, based on a first probability distribution indicating a distribution of a probability that the amount of change at a predetermined position of the cargo per unit time is a predetermined amount, which is a probability distribution based on the first data, a fluctuation value proportional to a force applied to the cargo by motor proteins that transport the cargo; and a force calculation unit configured to calculate the force based on the calculated fluctuation value.

Another aspect of the present invention is a force measurement system, including: a first acquisition unit configured to acquire first data indicating a temporal change of a position of cargo during a period in which the displacement of the cargo per unit time is substantially constant among data included in time course data indicating a movement trajectory of the cargo acquired in a non-invasive manner, a fluctuation value calculation unit configured to calculate, based on a first probability distribution indicating a distribution of a probability that the amount of change at a predetermined position of the cargo per unit time is a predetermined amount, which is a probability distribution based on the first data, a fluctuation value proportional to a force applied to the cargo by motor proteins that transport the cargo; and a force calculation unit configured to calculate the force based on the calculated fluctuation value.

Another aspect of the present invention is a force measurement program causing a computer to acquire first data indicating a temporal change of a position of cargo during a period in which the displacement of the cargo per unit time is substantially constant among data included in time course data indicating a movement trajectory of the cargo acquired in a non-invasive manner; to calculate, based on a first probability distribution indicating a distribution of a probability that the amount of change at a predetermined position of the cargo during unit time is a predetermined amount, which is a probability distribution based on the time course data, a fluctuation value proportional to a force applied to the cargo by motor proteins that transport the cargo; and calculate the force based on the calculated fluctuation value.

Another aspect of the present invention is a recording medium storing a program causing a computer: to acquire first data indicating a temporal change of a position of cargo during a period in which the displacement of the cargo per unit time is substantially constant among data included in time course data indicating a movement trajectory of the cargo acquired in a non-invasive manner; to calculate, based on a first probability distribution indicating a distribution of a probability that the amount of change at a predetermined position of the cargo during unit time is a predetermined amount, which is a probability distribution based on the time course data, a fluctuation value proportional to a force applied to the cargo by motor proteins that transport the cargo; and calculate the force based on the calculated fluctuation value.

Advantageous Effects of Invention

According to the present invention, a force applied to cargo in living cells can be measured in a non-invasive manner.

DESCRIPTION OF EMBODIMENTS (Principle)

In the present invention, when a physical quantity related to the force applied to cargo by the fluctuation theorem is measured, the force applied to the cargo is measured. Therefore, in description of the present invention, first, the fluctuation theorem will be described, and a principle in which a force applied to cargo is measured according to the present invention will be then described.

The fluctuation theorem is a theorem of nonequilibrium statistical mechanics, a field of physics, published in 1993, D. J. Evans et al. The fluctuation theorem is a theorem that links a predetermined physical quantity in a thermodynamically nonequilibrium system to a physical quantity that changes the predetermined physical quantity. The thermodynamically nonequilibrium system is, for example, a system in which cargo moves. In this case, the fluctuation theorem links the position of the cargo in the system to the force applied to the cargo. In this case, it is known that the fluctuation theorem that links the position of the cargo that moves and the force applied to the cargo that moves is represented by the following formula.

[Math. 1]

$$\frac{ln\left[\frac{P(\Delta X)}{P(-\Delta X)}\right]}{\Delta X} = AF \quad (1)$$

$\Delta X$ indicates an amount of displacement of the cargo per unit time, and $P(\Delta X)$ indicates a probability that an amount of displacement of the cargo is $\Delta X$. Here, $\Delta X$ is represented by the following Formula (2).

[Math. 2]

$$\Delta X = X(t+\Delta t) - X(t) \quad (2)$$

In Formula (2), $X(t)$ is a position of the cargo at the time t. In Formula (2), $X(t+\Delta t)$ is a position of the cargo at the time $t+\Delta t$.

In $\Delta X$, a force $F_c$ (denoted as F in Formula (1)) indicates a magnitude of a force applied to the cargo. A is a conversion coefficient for the physical quantity represented by the left side in Formula (1) and the force $F_c$. Hereinafter, the physical quantity represented by the left side in Formula (1) is a fluctuation value $\chi$, and A is a fluctuation coefficient. The fluctuation coefficient A is a unique value in a combination of the cargo and motor proteins.

When the amount of displacement of the cargo is measured, the fluctuation value $\chi$ is calculated. Therefore, when the fluctuation coefficient A is provided, the force $F_c$ applied to the cargo can be calculated by Formula (1).

Here, the amount of displacement of the cargo indicates the amount of change in the position of the cargo. In addition, the position of the cargo may be any position as long as it is a position of a part of the cargo, and may be, for example, the position of the center of gravity of the cargo.

Figure 1A:
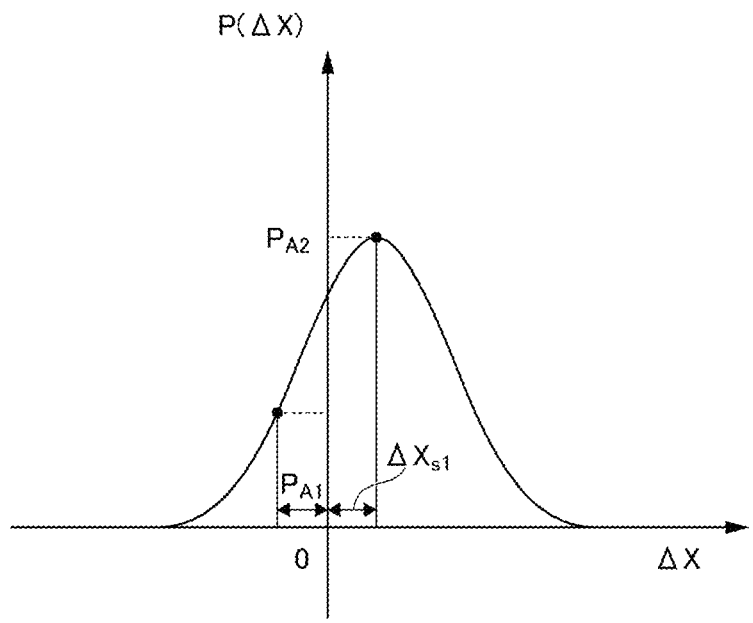
FIG. 1A is an explanatory diagram illustrating a case in which a fluctuation theorem reflects a force Fc.
Figure 1B:
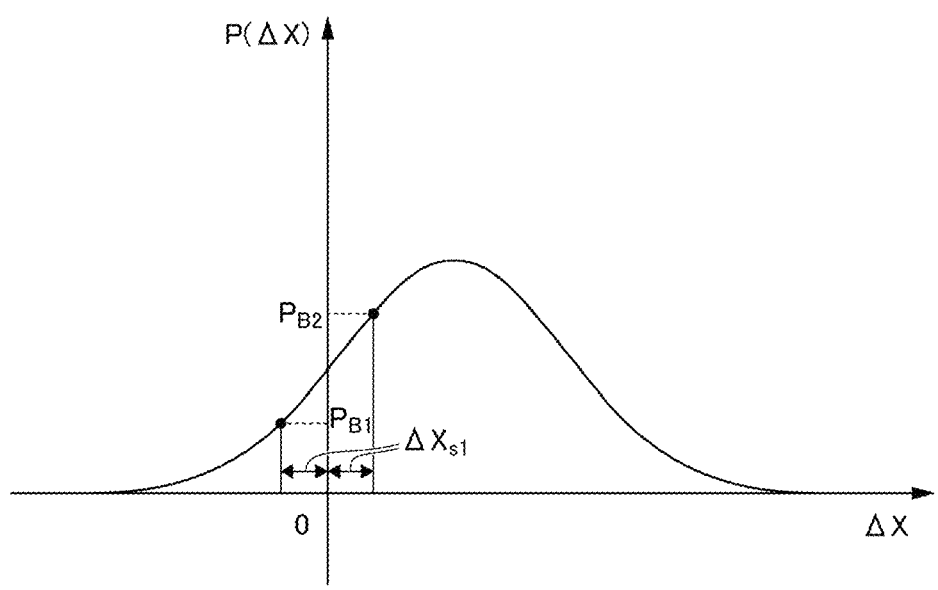
FIG. 1B is an explanatory diagram illustrating a case in which the fluctuation theorem reflects the force Fc.

FIG. 1A and FIG. 1B are explanatory diagrams illustrating a case in which the fluctuation theorem reflects the force $F_c$. Both FIG. 1A and FIG. 1B show a probability distribution of $\Delta X$ when a force is applied to the cargo. However, FIG. 1A shows a probability distribution of $\Delta X$ when a large amount of noise is applied to the cargo.

The probability distributions in FIG. 1A and FIG. 1B are, for example, both probability distributions according to a Gaussian distribution. Comparing FIG. 1A and FIG. 1B, in FIG. 1A, since the amount of noise applied to the cargo is small, the range of possible values of $\Delta X$ is narrower than the range of possible values of $\Delta X$ in FIG. 1B.

Therefore, the height of the peak of the probability distribution in FIG. 1A is lower than the height of the peak of the probability distribution in FIG. 1A. However, both ratios of P(ΔX) to P(−ΔX) are equal, which indicates that a ratio of P(ΔX) to P(−ΔX) reflects the force Fc rather than P(ΔX) itself. Therefore, the fluctuation theorem is referred to as a theorem that reflects the force $F_c$.

When the displacement of the cargo is measured, not only the value on the left side in Formula (1) but also the fluctuation coefficient A can be calculated. This will be described below. In cargo that moves in a viscous medium at a constant speed V, the force applied to the cargo by motor proteins and the viscous resistance force due to the medium match. Therefore, if the viscosity coefficient F of the medium is known, the force $F_c$ applied to the cargo by motor proteins can be calculated. Specifically, the force $F_c$ and the viscosity coefficient r satisfy the relationship of the following Formula (3).

[Math. 3]

$$F_c = \Gamma V \qquad (3)$$

Therefore, based on the fluctuation value χ and the force $F_c$ calculated based on the viscosity coefficient Γ, the fluctuation coefficient A is calculated. Here, the fluctuation coefficient A is a product of a Boltzmann constant $k_b$, and a temperature $T_{eff}$ (that is, the temperature is generally referred to as a nonequilibrium temperature or an effective temperature) of a system including cargo to be observed in the nonequilibrium state. The nonequilibrium state is a state in which the cargo is being transported.

In transport of the cargo according to motor proteins, $T_{eff}$ is a constant value. This has been experimentally verified.

Embodiment

Figure 2:
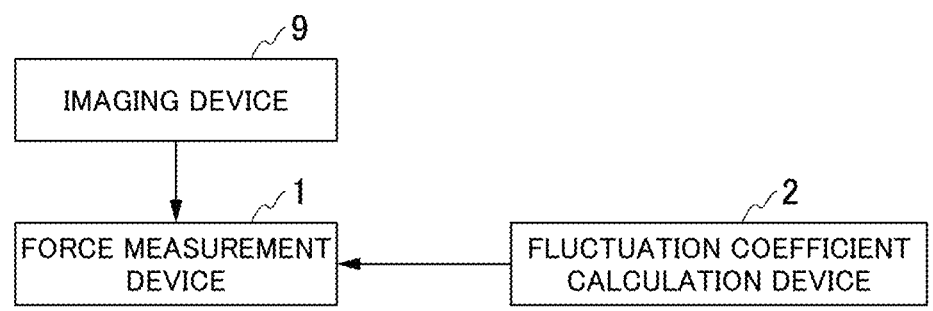
FIG. 2 is a diagram showing a specific example of a force measurement system 100 configured using a force measurement device 1 according to an embodiment.

FIG. 2 is a diagram showing a specific example of a force measurement system 100 configured using a force measurement device 1 according to an embodiment. The force measurement system 100 is a system that detects cargo in cells in a non-invasive manner, records movement of the cargo, and measures the force applied to the cargo. The force measurement system 100 includes the force measurement device 1, a fluctuation coefficient calculation device 2 and an imaging device 9.

Here, in the present invention, the cell to be observed has cargo and motor proteins and may be any cell as long as the motor proteins in the cell transport the cargo in the cell. Many generally known eukaryotic cells have such cargo and motor proteins. The observation subject is preferably neurons because in these the transport of cargo in the cell is easily observed. Examples of cells suitable as the observation subject other than neurons include glial cells, vascular endothelial cells, fibroblasts of skin or the like, melanocytes, generally used established animal cells, and egg cells.

In the present invention, the type of neurons to be observed is not particularly limited, and for example, neurons that can be cultured in vitro are preferable because it is easy to capture a video in these neurons. In addition, they may be cells that support neurons or cells in which other cells coexist. Examples of such cells include glial cells such as astrocytes, oligodendrocyte, and Schwann cells, vascular cells such as vascular epithelial cells, and mesenchymal cells such as fibroblasts. In addition, examples of such neurons include neurons that secrete an amino acid type neurotransmitter, neurons that secrete a peptide type neurotransmitter, and neurons that secrete monoamines or acetylcholine. When neurons are cultured, cells that support neurons may be allowed to coexist in order to simulate an in vivo environment. Examples of such accessory cells include glial cells such as astrocytes, oligodendrocyte, and Schwann cells.

In addition, in the present invention, the type of the cargo transported in cells to be observed is not particularly limited and may be any cargo of which fluctuation can be measured by an optical device. The presence or absence of a fluorescent label of the cargo when the fluctuation is measured is not limited. When the cargo is a vesicle or organelle covered with a lipid bilayer, it can be fluorescently labeled with a carbocyanine dye, for example, DiD, DiI, DiO, or DiR. Alternatively, proteins contained in the cargo can be fluorescently labeled with a fluorescent protein such as GFP. In addition, staining using a fluorescent dye and known labeling methods using biotin/avidin, antibodies, and the like can also be applied. The transport path of the cargo to be observed is not particularly limited, and may be axonal transport or other intracellular transports and can be appropriately selected according to the purpose of analysis.

The force measurement device 1 calculates a force Fe applied to the cargo to be observed based on a data group of images showing movement of the cargo to be observed. Hereinafter, a data group of images showing movement of the cargo to be observed will be referred to as observation data. The image showing movement of the cargo to be observed may be, for example, a 2D image. In addition, the observation data may be, for example, a video.

The fluctuation coefficient calculation device 2 calculates the fluctuation coefficient A of the cargo to be observed based on the observation data. The fluctuation coefficient calculation device 2 outputs the calculated fluctuation coefficient A to the force measurement device 1.

The imaging device 9 images the cargo to be observed in a non-invasive manner, and generates observation data in which movement of the cargo is recorded. The non-invasive manner may be, for example, a manner in which information on an observation subject is acquired with visible light. The information on an observation subject is, for example, a signal indicating the position of the center of gravity of the observation subject. In addition, the non-invasive manner may be, for example, a manner in which an observation subject is labeled with fluorescence to acquire information on an observation subject based on the fluorescence. These non-invasive manners may be realized using a microscope such as a fluorescence microscope or a differential interference microscope.

In addition, the non-invasive manner may be a manner in which information on an observation subject is acquired using a magnetic field with an intensity having little influence on the observation subject. Here, the invasive manner is, for example, a manner in which information on an observation subject is acquired by emitting a laser beam to an observation subject such as optical tweezers.

Here, a method of generating observation data in which movement of the cargo is recorded is not particularly limited, and for example, a known method using a confocal laser microscope including a commercially available digital video camera for cell dynamics observation may be used. In consideration of the speed of cargo axonal transport, and the like, an imaging frame rate is preferably about 10 to 100 frames/sec or more and particularly preferably 100 frames/sec.

In addition, in a process or manner of extracting an axon region in the captured image frame, various methods can be applied. For example, a method of visually determining an axon region is performed.

Figure 3:
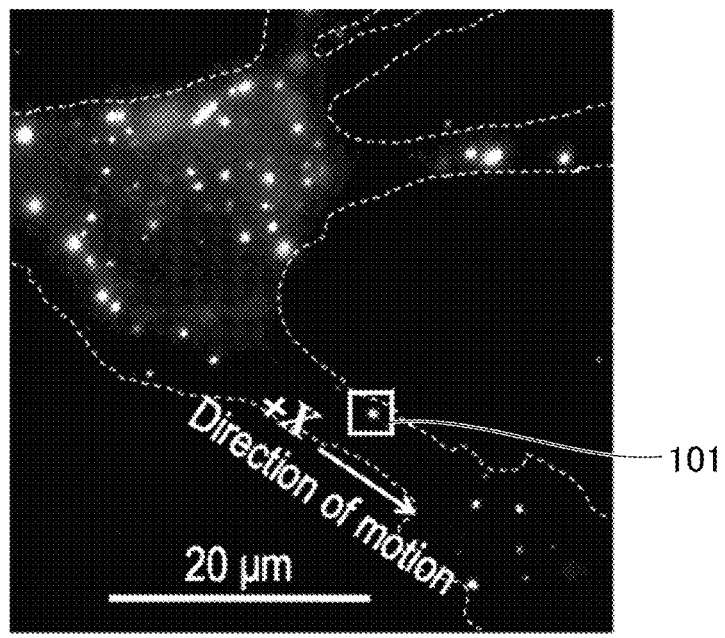
FIG. 3 is a diagram showing a specific example of observation data according to an embodiment.

FIG. 3 is a diagram showing a specific example of observation data according to an embodiment.

FIG. 3 is a 2D stationary image at a certain time t. A region surrounded by a dotted line in a stationary image in FIG. 3 represents an axon. In FIG. 3, a light emitting point in a region 101 surrounded by the line is cargo to be observed.

Figure 4:
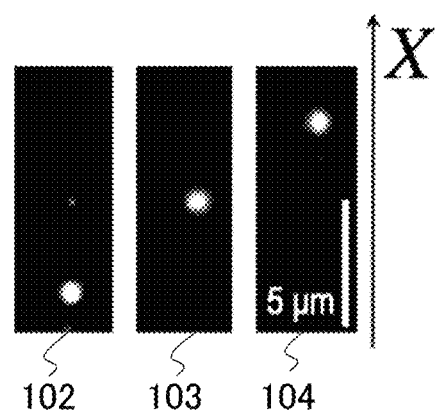
FIG. 4 is an explanatory diagram illustrating a case in which a plurality of pieces of observation data according to an embodiment indicate movement of an observation subject.

FIG. 4 is an explanatory diagram illustrating a case in which a plurality of pieces of observation data according to an embodiment indicate movement of an observation subject.

In FIG. 4, an image 102 shows the position of the cargo to be observed at the time t=0 s.

Here, the cargo to be observed is cargo to be observed in the region 101 in FIG. 3. In FIG. 4, an image 103 shows the position of the cargo to be observed at a time after 0 s and before 1.8 s. In FIG. 4, an image 104 shows the position of the cargo to be observed at the time t=1.8 s.

The observation data is a data group including a plurality of 2D stationary images shown in FIG. 3 at different times. Therefore, the observation data indicates movement of the cargo to be observed as shown in FIG. 4 based on data of stationary images at different times that the observation data includes.

Figure 5:
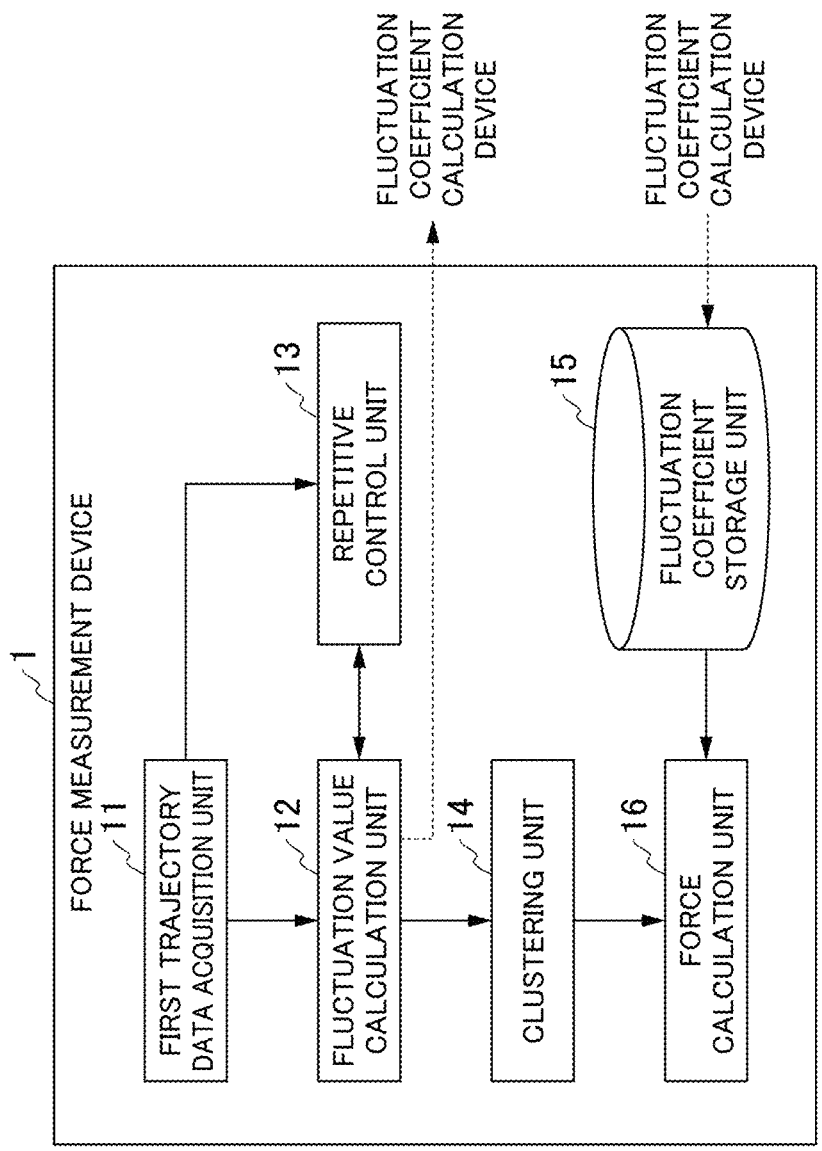
FIG. 5 is a diagram showing a specific example of a functional configuration of the force measurement device 1 according to the embodiment.

FIG. 5 is a diagram showing a specific example of a functional configuration of the force measurement device 1 according to an embodiment. The force measurement device 1 includes a first trajectory data acquisition unit 11, a fluctuation value calculation unit 12, a repetitive control unit 13, a clustering unit 14, a fluctuation coefficient storage unit 15, and a force calculation unit 16.

The first trajectory data acquisition unit 11 acquires time course data including constant speed movement data generated based on observation data. The time course data is data indicating projection of the observation subject indicated by observation data on one predetermined axis of a trajectory and is a set of data having two values of a time t and a position X of the cargo at the time t. The one predetermined axis may be any axis, and may be, for example, an axis parallel to a direction in which the cargo is transported. In addition, the constant speed movement data is data included in time course data and is data indicating a temporal change of the position of the cargo during a period in which the displacement of the cargo per unit time is substantially constant (hereinafter referred to as a "constant speed period"). That is, the constant speed movement data is data indicating a temporal change of the position of the cargo during a period in which the cargo moves at a substantially constant speed. The constant speed movement data is also a set of data having two values of the time t and the position X of the cargo.

Figure 6:
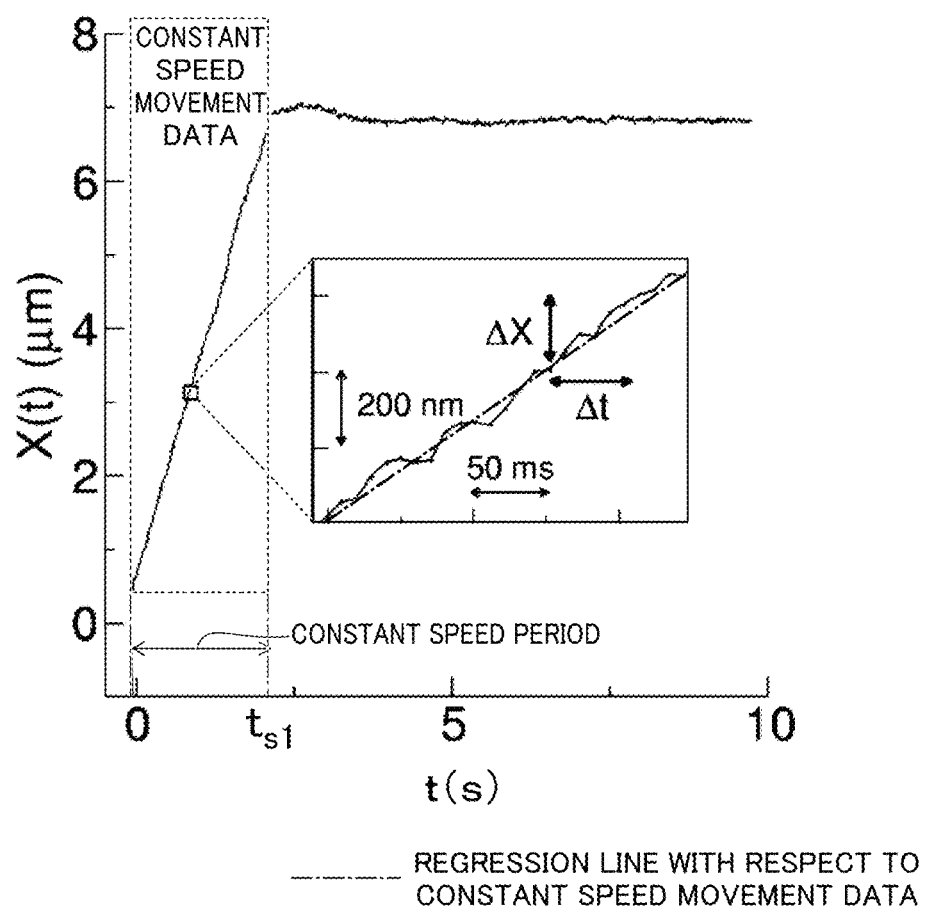
FIG. 6 is a diagram showing a specific example of time course data, constant speed movement data and a constant speed period according to an embodiment.

FIG. 6 is a diagram showing a specific example of time course data, constant speed movement data and a constant speed period according to an embodiment.

The graph in FIG. 6 shows time course data indicating the position X of the cargo during a time from the time t=0 s to the t=10 s. In FIG. 6, the horizontal axis represents time, and the vertical axis represents the position X of the cargo. In FIG. 6, X on the vertical axis is expressed as X(t) in order to specify the position X that depends on the time t. In FIG. 6, data during a period from the time 0 to the time $t_{s1}$ is data indicating that the cargo to be observed moves at a substantially constant speed and is a specific example of constant speed movement data. In addition, the period from the time 0 to the time $t_{s1}$ is a specific example of the constant speed period. FIG. 6 also shows an enlarged view of part of the graph showing constant speed movement data. The straight line in the enlarged view is a regression line for constant speed movement data. The regression line indicates that the cargo moves at a constant speed in a direction in which the value of X increases. The enlarged view shows that the movement speed of the cargo is not constant in a short time of 50 ms or less, and the cargo moves at a speed having a fluctuation of a position of 200 nm or less in 50 ms.

The description will return to FIG. 5. The fluctuation value calculation unit 12 calculates a fluctuation value $\chi$ based on constant speed movement data. Specifically, the fluctuation value calculation unit 12 calculates a fluctuation value by performing a fluctuation value calculation process after a first probability distribution calculation process is performed. Hereinafter, specific processing details of the first probability distribution calculation process and the fluctuation value calculation process will be described. First, the first probability distribution calculation process will be described.

The first probability distribution calculation process is a process of calculating a probability distribution of the amount of displacement $\Delta X$ of the position of the cargo in the unit time $\Delta t$ during a constant speed period based on one piece of constant speed movement data. Specifically, in the first probability distribution calculation process, first, the amount of displacement $\Delta X_n = X_n - X_{(n-1)}$ of the position of the cargo is acquired for various n when the time origin in constant speed movement data is $t_0$, the position of the cargo at the time origin $t_0$ is $X_0$, and the position of the cargo at the time $t_0 + n \times \Delta t$ (n is an integer) is $X_n$. Hereinafter, a process of acquiring the amount of displacement $\Delta X_n$ of the position of the cargo for various n is referred to as a displacement amount calculation process. Next, in the first probability distribution calculation process, a probability distribution (hereinafter referred to as a "first probability distribution") in which the value of the amount of displacement $\Delta X$ of the position of the cargo is $\Delta X_n$ is calculated.

Figure 7:
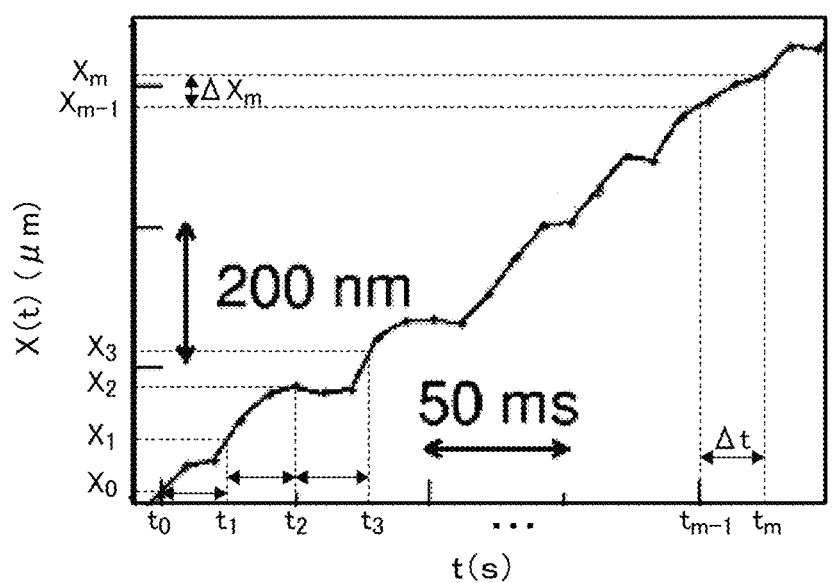
FIG. 7 is an explanatory diagram illustrating a specific procedure of a displacement amount calculation process in a first probability distribution calculation process according to an embodiment.

FIG. 7 is an explanatory diagram illustrating a specific procedure of the displacement amount calculation process in the first probability distribution calculation process according to an embodiment.

The graph in FIG. 7 is a graph in an enlarged view of a part of the time course data in FIG. 6. In FIG. 7, first, the fluctuation value calculation unit 12 performs the displacement amount calculation process and thus acquires the position (that is, $X_0, X_1, X_2, \ldots X_m$) of the cargo from the time $t_0$ to the time $t_m$ at every predetermined unit time $\Delta t$. Next, the fluctuation value calculation unit 12 performs the displacement amount calculation process and thus calculates an amount of displacement of the position of the cargo. That is, $\Delta X_1 = X_1 - X_0, \Delta X_2 = X_2 - X_1, \Delta X_3 = X_3 - X_2, \ldots \Delta X_m = X_m - X_{m-1}$ are calculated. In this manner, the fluctuation value calculation unit 12 acquires the position of the cargo from the time $t_0$ to the time $t_m$ at every predetermined unit time $\Delta t$.

The description will return to FIG. 5. The fluctuation value calculation process that is performed by the fluctuation value calculation unit 12 will be described. The fluctuation value calculation unit 12 calculates a fluctuation value $\chi$ based on the first probability distribution and Formula (1) according to the fluctuation value calculation process. As described above, the fluctuation value $\chi$ is a physical quantity represented by the left side in Formula (1). In the fluctuation value calculation process, a value that is assigned to $P(\Delta X)$ on the left side in Formula (1) is a value of a probability represented by the first probability distribution and is a value of a probability that the amount of displacement of the position of the cargo is $\Delta X$.

The repetitive control unit 13 controls the fluctuation value calculation unit 12 so that a plurality of fluctuation values $\chi$ are calculated. Specifically, first, the repetitive control unit 13 controls the fluctuation value calculation unit 12 so that the a fluctuation value $\chi$ is calculated at a plurality of predetermined unit times $\Delta t$ from the shortest unit time to the longest unit time with respect to one piece of constant speed movement data. Hereinafter, this control is referred to as unit temporal change repetitive control. The longest unit time is a predetermined time that is determined in advance by a user and is the shortest time among possible times of the unit time $\Delta t$. The longest unit time is a predetermined time that is determined in advance by a user and the longest time among possible times of the unit time $\Delta t$. The shortest unit time may be, for example, 10 ms. The longest unit time may be, for example, 100 ms. In addition, the unit time may be, for example, 50 ms. In addition, the repetitive control unit 13 performs unit temporal change repetitive control on the time course data including constant speed movement data acquired by the first trajectory data acquisition unit 11.

Here, the unit temporal change repetitive control may be, for example, a control in which the fluctuation value calculation unit 12 is controlled so that the fluctuation value $\chi$ is calculated at each $\Delta t$ in order from the shorter unit time $\Delta t$ from the shortest unit time to the longest unit time.

Figure 8:
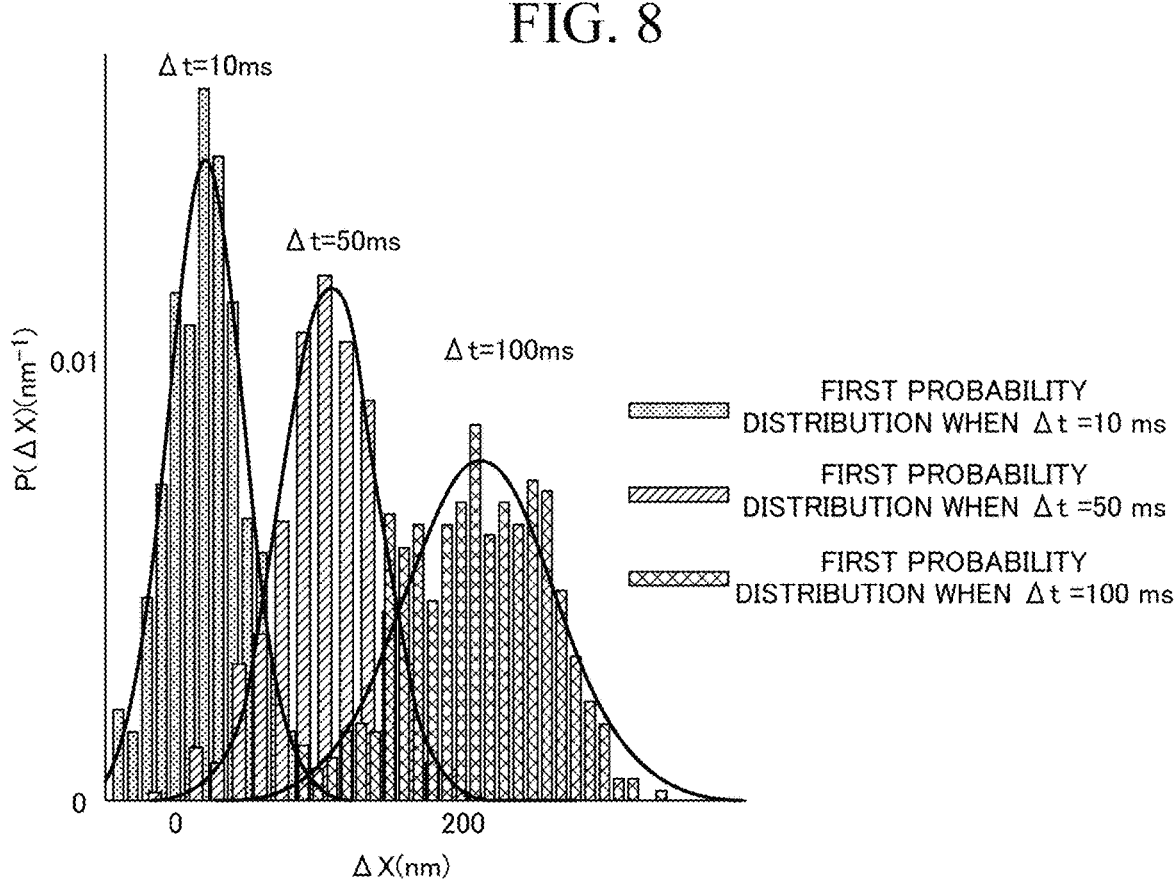
FIG. 8 is a diagram showing specific calculation results of a first probability distribution according to an embodiment.
Figure 9:
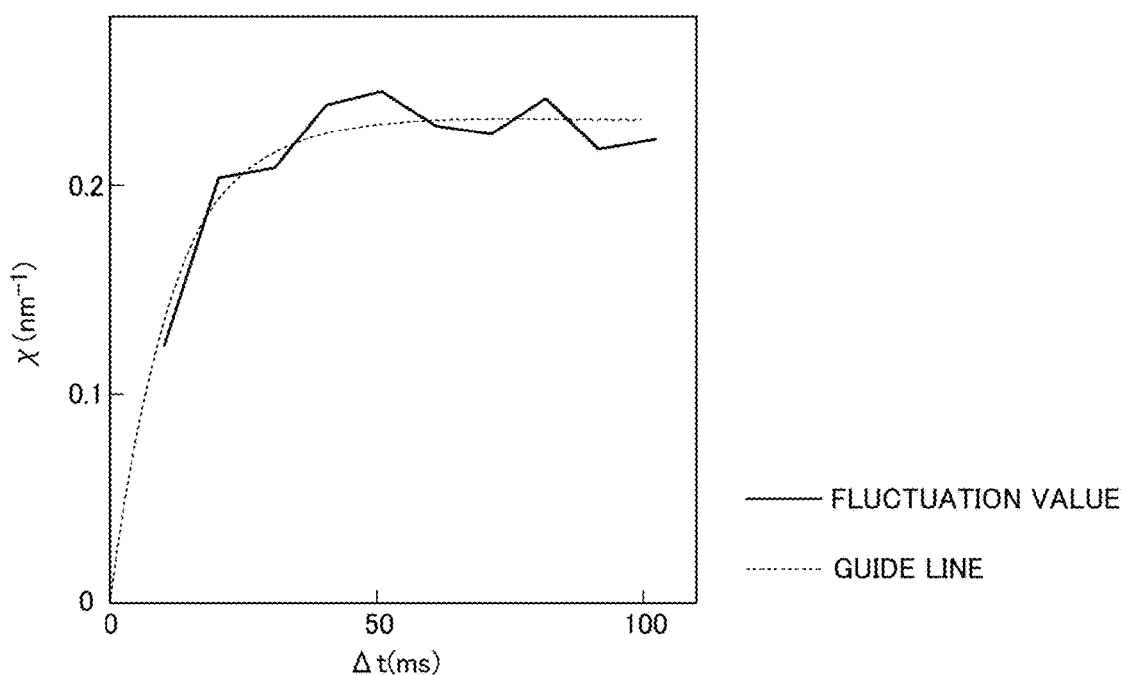
FIG. 9 is a diagram showing specific calculation results of a fluctuation value $\chi$ according to an embodiment.

FIG. 8 and FIG. 9 show specific examples of a first probability distribution and a fluctuation value $\chi$ calculated by the fluctuation value calculation unit 12 and the repetitive control unit 13.

FIG. 8 is a diagram showing specific calculation results of a first probability distribution according to an embodiment. FIG. 8 shows a first probability distribution when the unit time $\Delta t$ is 10 ms, 50 ms or 100 ms. In the first probability distribution, when the unit time $\Delta t$ becomes longer, the peak moves in a direction in which the value of $\Delta X$ at the peak of the distribution becomes larger. This result is obtained because the cargo moves at a constant speed, and obtained because the distance that the cargo moves is longer when the time is longer. In addition, the variance of the first probability distribution increases as the unit time $\Delta t$ increases. This result is obtained because the distance that the cargo moves is longer when the time is longer, and the variation in the amount of displacement of the cargo per unit time increases.

FIG. 9 is a diagram showing specific calculation results of a fluctuation value $\chi$ according to an embodiment. More specifically, FIG. 9 is a graph showing the value of $\chi$ for each of a plurality of unit times $\Delta t$ with respect to one piece of time course data. FIG. 9 shows a graph in which the fluctuation value $\chi$ converges to a constant value as the unit time $\Delta t$ increases. The result in which the fluctuation value $\chi$ converges to a constant value as $\Delta t$ increases is a result in which relaxation of a system is reflected. Relaxation of the system means that the system including the cargo to be observed is relaxed in an equilibrium state. Relaxation is caused by microscopic movement of substances contained in the system, ATP hydrolysis of motor proteins in the system, and the like.

The description will return to FIG. 5. The clustering unit 14 performs clustering on the plurality of fluctuation values $\chi$ calculated by the fluctuation value calculation unit 12, and outputs a value of $\chi$ in which the variation in measurement is reduced. Here, the variation related to measurement is, for example, a variation in acquired data caused by a change in the temperature, humidity or the like of a system including an observation subject during measurement, a vibration in a measurement device, or the like. Specifically, first, the clustering unit 14 performs clustering on the plurality of fluctuation values $\chi$ calculated by the fluctuation value calculation unit 12 under control of the repetitive control unit 13 and classifies the fluctuation values $\chi$. The clustering may be performed by any clustering method as long as it has a reference value for automatically estimating the number of clusters. For example, a k-means method involving calculation of Akaike's Information Criterion (AIC) as a reference value may be used. The reference value for automatically estimating the number of clusters is not limited to AIC, for example, a reference value such as a Bayesian information criterion (BIC) and a minimum description length (MDL) may be used. The clustering method is not limited to the k-means method, and may be, for example, a k-means++ method.

Next, the clustering unit 14 outputs the representative value of the result of clustering as $\chi$ in which the variation in measurement is reduced. Here, the representative value may be any value as long as the value represents a cluster for each clustering method, and may be, for example, an average value or a median value.

Figure 10:
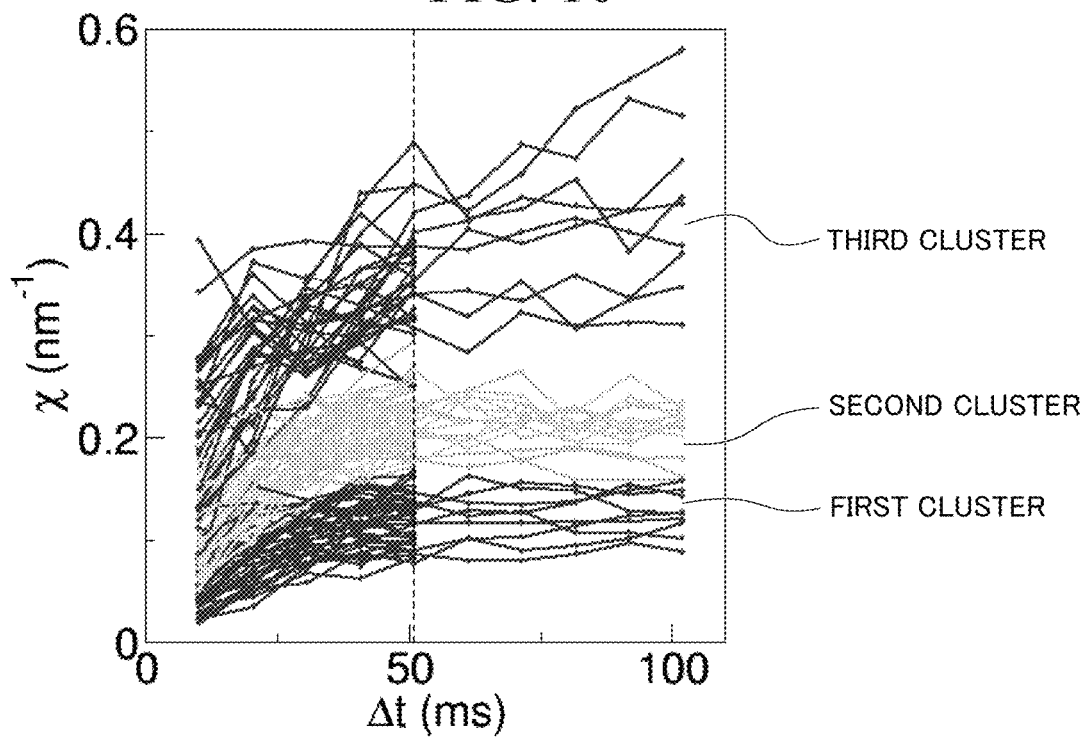
FIG. 10 is a diagram showing a fluctuation value $\chi$ clustered by a clustering unit 14 according to an embodiment.

FIG. 10 is a diagram showing the fluctuation value $\chi$ clustered by the clustering unit 14 according to an embodiment. FIG. 10 shows three clusters (that is, first to third clusters) of which representative values are discretized. The magnitude of the fluctuation value $\chi$ belonging to the first cluster is a value of 0 or more and 0.2 or less at $\Delta t=100$ ms. The magnitude of the fluctuation value $\chi$ belonging to the second cluster is a value of 0.1 or more and 0.2 or less at $\Delta t=100$ ms. The magnitude of the fluctuation value $\chi$ belonging to the third cluster is a value of 0.3 or more and 0.6 or less at $\Delta t=100$ ms. Here, the representative values in FIG. 10 are average values. The representative values of the first to third clusters are, in ascending order, the representative value of the first cluster, the representative value of the second cluster, and the representative value of the third cluster. In addition, the representative value of the second cluster and the representative value of the third cluster are each an integral multiple of the representative value of the first cluster.

The fluctuation coefficient storage unit 15 stores the fluctuation coefficient A calculated by the fluctuation coefficient calculation device 2.

The fluctuation coefficient storage unit 15 is configured using a storage device such as a magnetic hard disk drive and a semiconductor storage device.

The force calculation unit 16 calculates a force Fe applied to the cargo to be observed based on the fluctuation value $\chi$ and the fluctuation coefficient A. Specifically, $F_c$ is calculated using Formula (1) and the fact that the right side of Formula (1) is $\chi$.

Figure 11:
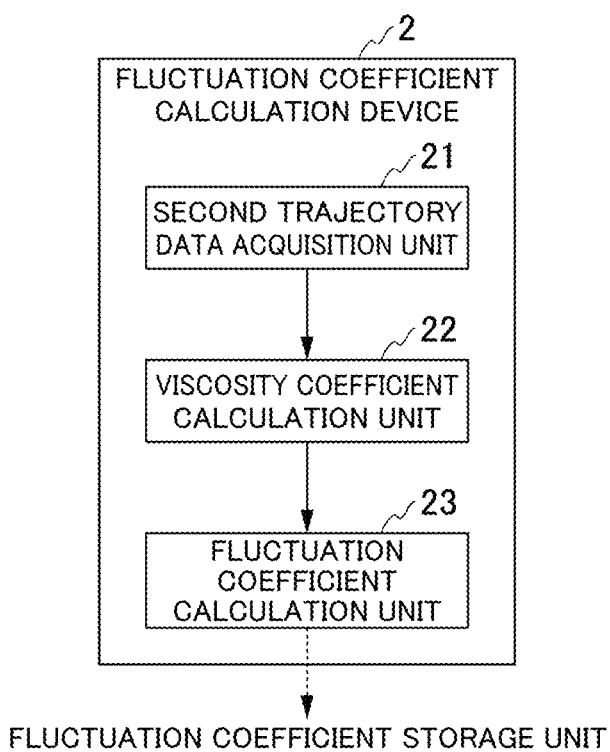
FIG. 11 is a diagram showing a specific example of a functional configuration of a fluctuation coefficient calculation device 2 according to an embodiment.

FIG. 11 is a diagram showing a specific example of a functional configuration of the fluctuation coefficient calculation device 2 according to an embodiment. The fluctuation coefficient calculation device 2 includes a second trajectory data acquisition unit 21, a viscosity coefficient calculation unit 22, and a fluctuation coefficient calculation unit 23.

The second trajectory data acquisition unit 21 acquires time course data including constant speed movement data and stationary data generated based on observation data. The stationary data is data included in the time course and is data indicating a temporal change in the position of the cargo during a period in which the position of the cargo is substantially the same position regardless of time (hereinafter referred to as "stationary period"). That is, the stationary data is data indicating a temporal change of the position of the cargo during a period in which the cargo remains at the same position regardless of time. Like the time course data, the stationary data is a set of data having two values of the time t and the position X of the cargo. Here, among the time course data including constant speed movement data, a proportion of time course data including not only constant speed movement data but also stationary data is about 10%.

Figure 12:
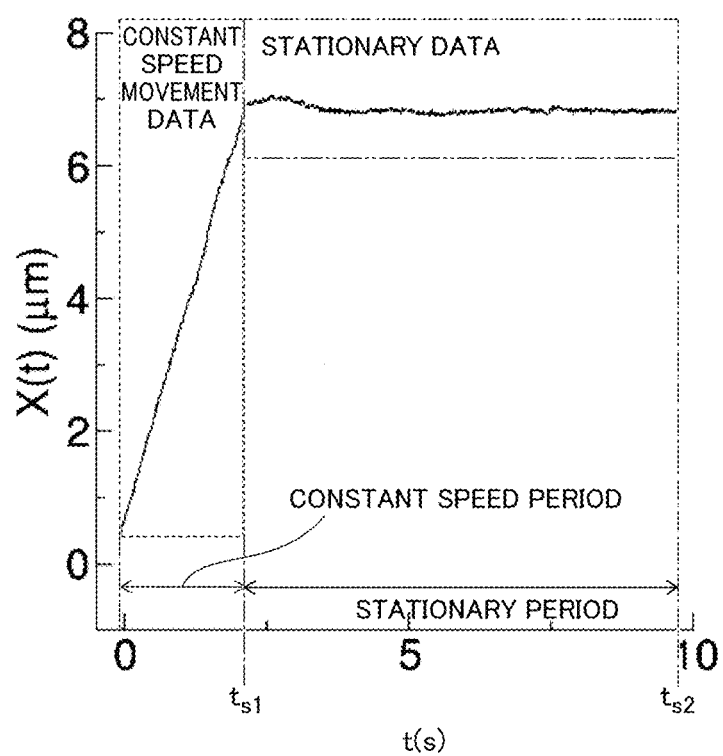
FIG. 12 is a diagram showing a specific example of time course data including stationary data and constant speed movement data according to an embodiment.

FIG. 12 is a diagram showing a specific example of time course data including stationary data and constant speed movement data according to an embodiment.

The graph in FIG. 12 is a graph similar to the graph in FIG. 6 and is a graph showing time course data indicating the position X of the cargo during a period from the time t=0 s to t=10 s. In FIG. 12, the horizontal axis represents time, and the vertical axis represents the position X of the cargo. In FIG. 12, like FIG. 6, X on the vertical axis is expressed as X(t) in order to specify the position X that depends on the time t. In FIG. 12, data during a period from the time $t_{s1}$ to the time $t_{s2}$ is data indicating that the cargo to be observed remains at the same position regardless of time. That is, data during a period from the time $t_{s1}$ to the time $t_{s2}$ in FIG. 12 is a specific example of stationary data. In addition, the period from the time $t_{s1}$ to the time $t_{s2}$ is a specific example of the stationary period. Here, data during a period from the time 0 to the time $t_{s1}$ is a specific example of the constant speed movement data similar to that in FIG. 5.

The description will return to FIG. 11. The viscosity coefficient calculation unit 22 calculates a viscosity coefficient based on stationary data. Specifically, the viscosity coefficient calculation unit 22 calculates a viscosity coefficient by sequentially performing a second probability distribution calculation process, a distribution coefficient calculation process, a power spectrum calculation process, a power coefficient calculation process and a viscosity coefficient calculation process.

The second probability distribution calculation process is a process of calculating a probability distribution (hereinafter referred to as a "second probability distribution") of the position X of the cargo at the time t during the stationary period based on one piece of stationary data. The second probability distribution is a distribution according to the Boltzmann distribution.

In the distribution coefficient calculation process, fitting is performed on the second probability distribution calculated in the second probability distribution calculation process using a Boltzmann function $P_B(X)$, which is a function including K as a fitting parameter, and the value of the fitting parameter K is calculated. A specific function form of the Boltzmann function $P_B(X)$ is a function form represented by Formula (4). Hereinafter, the fitting parameter K will be referred to as a distribution coefficient. Here, the fitting may be performed by any fitting method, for example, a least squares method.

[Math. 4]

$$P_B(X) = \frac{\exp\left(\frac{-Kk_bTX^2}{2}\right)}{Z} \tag{4}$$

$P_B(X)$ represents a probability that the position of the cargo is X. Z and T represent a distribution function and the temperature of an environment. The temperature of the environment is a temperature of a medium surrounding the cargo to be observed.

The power spectrum calculation process is a process of Fourier-transforming the second probability distribution according to the frequency ν and calculating a power spectrum.

The power coefficient calculation process is a process in which the power spectrum is fitted using a Lorentzian function g(ν) including $A_p$ and $B_p$ as fitting parameters and a fitting parameter $B_p$ is calculated. A specific function form of the function g(ν) is a function form represented by Formula (5). Hereinafter, the fitting parameter $B_p$ will be referred to as a power coefficient. The fitting may be performed by any fitting method, for example, a least squares method.

[Math. 5]

$$g(v) = \frac{A_p}{(1 + (B_p v)^2)} \tag{5}$$

The viscosity coefficient calculation process is a process of calculating a viscosity coefficient Γ represented by the following Formula (6) using the distribution coefficient K and the power coefficient $B_p$.

[Math. 6]

$$\Gamma = KB_p \tag{6}$$

The fluctuation coefficient calculation unit 23 calculates the fluctuation coefficient A based on the viscosity coefficient Γ and the fluctuation value χ. The viscosity coefficient calculation unit calculates a fluctuation coefficient A by sequentially performing a speed calculation process and a fluctuation coefficient calculation process.

The speed calculation process is a process of calculating a time average speed V of the cargo during a constant speed movement period using constant speed movement data of time course data including stationary data. Specifically, the speed calculation process is a process of calculating a slope of a regression line of constant speed movement data in a graph in which the horizontal axis represents time and the vertical axis represents the position of the cargo.

The fluctuation coefficient calculation process is a process of calculating a fluctuation coefficient A based on the speed V, the viscosity coefficient Γ and the fluctuation value χ. In the fluctuation coefficient calculation process, first, the fluctuation coefficient calculation unit 23 acquires data having two values of the force $F_c$ calculated by Formula (3) and the fluctuation value χ calculated by the fluctuation value calculation unit 12 (hereinafter referred to as "force fluctuation value correspondence data") for a plurality of pieces of time course data including stationary data and constant speed movement data. Next, in the fluctuation coefficient calculation process, the fluctuation coefficient calculation unit 23 fits the acquired plurality of pieces of force fluctuation value correspondence data using a linear function represented by the following Formula (7) including a fitting parameter $A_1$.

[Math. 7]

$$F_c = A_1 \chi \tag{7}$$

$A_1$ is a fitting parameter, and the value of $A_1$ obtained by fitting is a fluctuation coefficient A. It is clear from Formula (1) and Formula (6) that the value of $A_1$ obtained by fitting is the fluctuation coefficient A.

Figure 13:
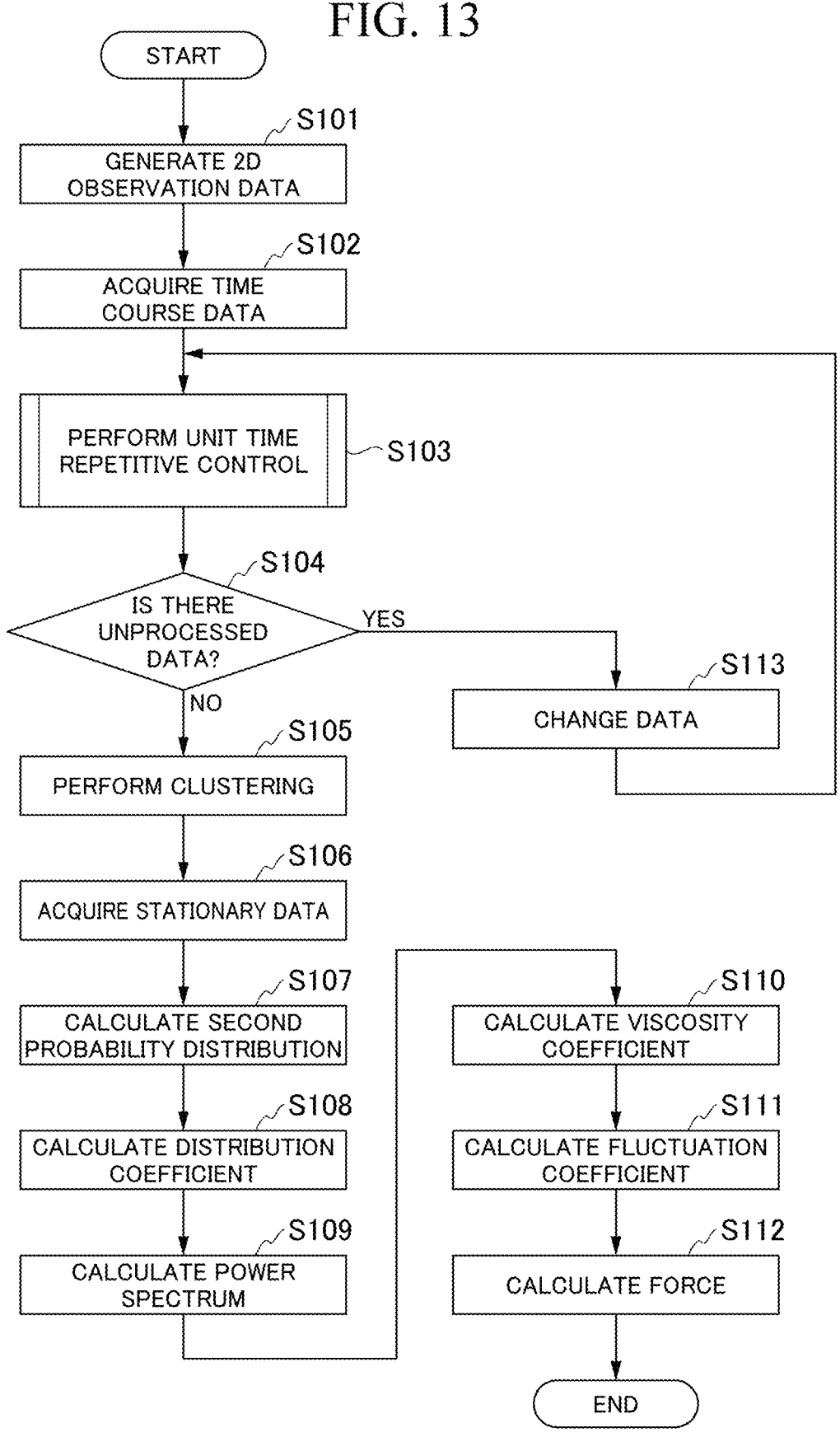
FIG. 13 is a flowchart showing a flow of a specific process of calculating a force applied to motor proteins by the force measurement device 1 according to the embodiment.

FIG. 13 is a flowchart showing a flow of a specific process of calculating a force applied to motor proteins by the force measurement device 1 according to an embodiment.

The imaging device 9 generates observation data of the cargo to be observed (Step S101). The first trajectory data acquisition unit 11 acquires time course data including constant speed movement data generated based on observation data acquired by the imaging device 9 (Step S102). The repetitive control unit 13 performs unit time repetitive control on one piece (hereinafter referred to as "data to be calculated") of time course data including constant speed movement data at a plurality of predetermined unit times Δt and thus calculates the fluctuation value $\chi$ at the plurality of unit times Δt (Step S103).

The repetitive control unit 13 determines whether there is time course data on which the first probability distribution calculation process has not been performed among time course data including constant speed movement data acquired by the first trajectory data acquisition unit 11 (Step S104). When there is no time course data on which the first probability distribution calculation process has not been performed (No in Step S104), the clustering unit 14 performs clustering on the fluctuation value $\chi$ and calculates a fluctuation value $\chi$ in which the variation in measurement is reduced (Step S105).

After the clustering unit 14 calculates the fluctuation value $\chi$ in which the variation related to measurement is reduced, the second trajectory data acquisition unit 21 acquires time course data including stationary data and constant speed movement data (Step S106). After the second trajectory data acquisition unit 21 acquires time course data including stationary data and constant speed movement data, the viscosity coefficient calculation unit 22 performs the second probability distribution calculation process, and thus calculates a second probability distribution based on the stationary data acquired by the second trajectory data acquisition unit 21 (Step S107). After the second probability distribution is calculated, the viscosity coefficient calculation unit 22 performs the distribution coefficient calculation process on the second probability distribution and calculates the value of the distribution coefficient K in the Boltzmann function $P_B(X)$ represented by Formula (4) (Step S108). The viscosity coefficient calculation unit 22 that has calculated the distribution coefficient K performs the power spectrum calculation process on the second probability distribution and calculates a power spectrum (Step S109). The viscosity coefficient calculation unit 22 that has calculated the power spectrum performs the viscosity coefficient calculation process and calculates a viscosity coefficient Γ (Step S110).

After the viscosity coefficient calculation unit 22 calculates a viscosity coefficient Γ, the fluctuation coefficient calculation unit 23 performs the fluctuation coefficient calculation process and calculates a fluctuation coefficient A (Step S111). After the fluctuation coefficient A is calculated, the force calculation unit 16 calculates a force $F_c$ applied to the cargo based on $\chi$ calculated in Step S105 and the fluctuation coefficient A calculated in Step S111 (Step S112).

On the other hand, in Step S104, when there is time course data on which the first probability distribution calculation process has not been performed (Yes in Step S104), the repetitive control unit 13 sets the time course data as new data to be calculated (Step S113). The repetitive control unit 13 performs unit time repetitive control on new data to be calculated (Step S103).

Here, Steps S106 to 110 need not necessarily be performed after Step 107, and may be performed in parallel with Steps S103 to 105, or may be performed before Steps S103 to 105.

Figure 14:
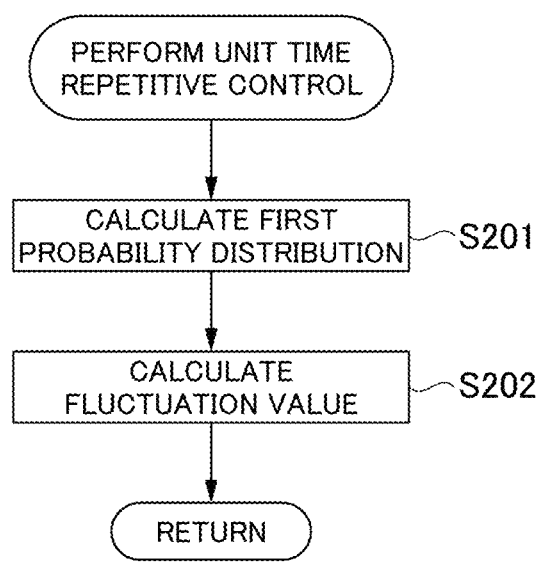
FIG. 14 is a flowchart showing a flow of a specific process of unit time repetitive control (Step S103) according to an embodiment.

FIG. 14 is a flowchart showing a flow of a specific process of unit time repetitive control (Step S103) according to an embodiment. The fluctuation value calculation unit 12 acquires the time course data acquired by the first trajectory data acquisition unit 11 and performs the first probability distribution calculation process (Step S201). The fluctuation value calculation unit 12 performs the first probability distribution calculation process and thus calculates a first probability distribution. The fluctuation value calculation unit 12 that has calculated the first probability distribution performs the fluctuation value calculation process and thus calculates a fluctuation value $\chi$ (Step S202).

Since the force measurement device 1 of the embodiment configured in this manner includes the fluctuation value calculation unit 12 that calculates the value $\chi$ proportional to the force $F_c$ applied to the cargo to be observed based on a 2D image data group indicating movement of the cargo, the user can measure the force applied to cargo in living cells in a non-invasive manner.

(Method of Culturing Neurons (Example))

The superior cervical ganglion was collected from 3-week old ICR mice (male) and treated with an enzyme such as 0.5% trypsin and 0.5% collagenase. neurons separated individually were rinsed with a DMEM/F12 medium containing a 10% h inactivated bovine serum, and then spread on a matrigel-coated glass bottom dish. The neurons were cultured in a DMEM/F12 medium containing a 10% inactivated bovine serum and a 200 ng/ml 2.5 S nerve growth factor in an incubator at 37° C. and $CO_2$ 5% for 2 to 4 days and used for an experiment using the force measurement device 1.

(Method of Staining Organelles (Example: Endosome))

A fluorescent dye DiI was added to a medium of neurons during culturing so that the final concentration was 100 nM, and staining was performed for 10 minutes, and the result was then used for fluorescence observation.

(Method of Fluorescence Observation (Example))

The dish after stain was placed on a heating plate (CU-201, Live Cell Instrument), and the stained melanin vesicles in melanocytes were observed under a dark-field microscope (IX71, Olympus) while the temperature was maintained at 37° C. A video was captured using an EMCCD camera (LucaS (Andor)) with a 100× objective lens (UPlanFL 100x/1.3, Plympus) at 98 frames per second. Time course data of the position of the center of gravity of melanin vesicles was calculated from the video using ImageJ (Rasband, 1997).

Figure 15A:
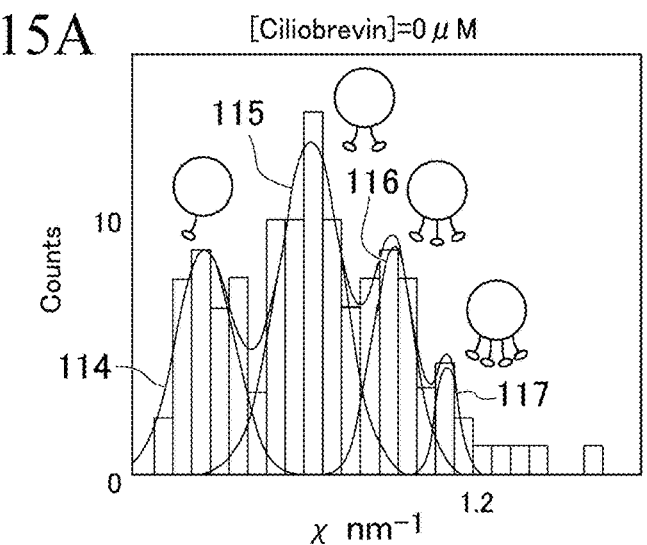
FIG. 15A is a diagram showing specific results showing that the fact that the frequency distribution of the fluctuation value $\chi$ changes according to addition of Ciliobrevin to cells becomes clear from measurement of $\chi$ using the force measurement device 1 of the embodiment.
Figure 15B:
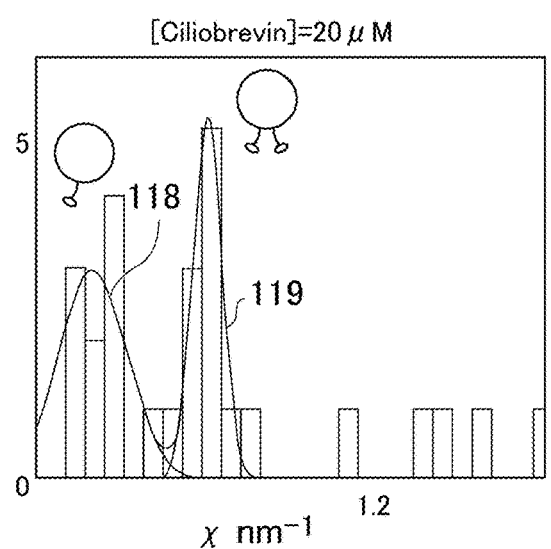
FIG. 15B is a diagram showing specific results showing that the fact that the frequency distribution of the fluctuation value $\chi$ changes according to addition of Ciliobrevin to cells becomes clear from measurement of $\chi$ using the force measurement device 1 of the embodiment.
Figure 15C:
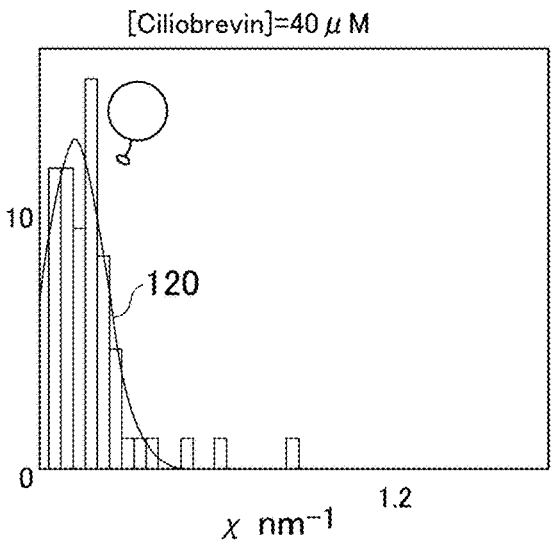
FIG. 15C is a diagram showing specific results showing that the fact that the frequency distribution of the fluctuation value $\chi$ changes according to addition of Ciliobrevin to cells becomes clear from measurement of $\chi$ using the force measurement device 1 of the embodiment.

FIG. 15A, FIG. 15B and FIG. 15C are diagrams showing specific results showing that the fact that the frequency distribution of the fluctuation value $\chi$ changes according to addition of Ciliobrevin which is a reagent that inhibits a function of motor proteins into melanocytes is clear from measurement of $\chi$ using the force measurement device 1 of the embodiment.

FIG. 15A is a diagram showing the frequency distribution of the fluctuation value $\chi$ measured by the force measurement device 1 when Ciliobrevin was not added to cells. In FIG. 15A, for $\chi$, the distribution of data is classified into four clusters (clusters 114 to 117).

FIG. 15B is a diagram showing the frequency distribution of the fluctuation value $\chi$ measured by the force measurement device 1 when the concentration of Ciliobrevin in the cell culture medium was 20 μM. In FIG. 15B, for χ, the distribution of data is classified into two clusters (clusters 118 and 119).

FIG. 15C is a diagram showing the frequency distribution of the fluctuation value χ measured by the force measurement device 1 when the concentration of Ciliobrevin in the cell culture medium was 40 μM. In FIG. 15C, in χ, the distribution of data is classified into one cluster 120.

Comparing FIG. 15A with FIG. 15B and FIG. 15C, it shows that the number of clusters decreases as the amount of Ciliobrevin added increases.

Figure 16A:
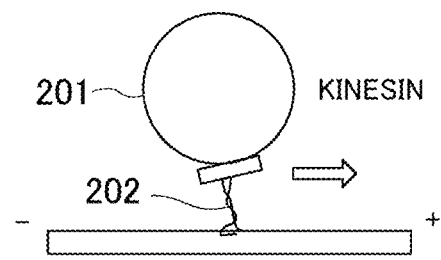
FIG. 16A is an explanatory diagram illustrating a case in which an endosome is transported between a cell center and a cell membrane by kinesin.
Figure 16B:
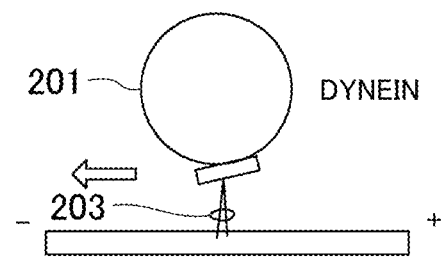
FIG. 16B is an explanatory diagram illustrating a case in which an endosome is transported between a cell center and a cell membrane by dynein.

FIG. 16A and FIG. 16B are explanatory diagrams illustrating cases in which an endosome is transported between a cell center and a cell membrane by a kinesin or dynein.

FIG. 16A shows a case in which an endosome 201 is transported along microtubules from a cell center to a cell membrane by a kinesin 202 that binds to the endosome 201.

FIG. 16B shows a case in which an endosome 201 is transported along microtubules from a cell membrane to a cell center by a dynein 203 that binds to the endosome 201.

Figure 17A:
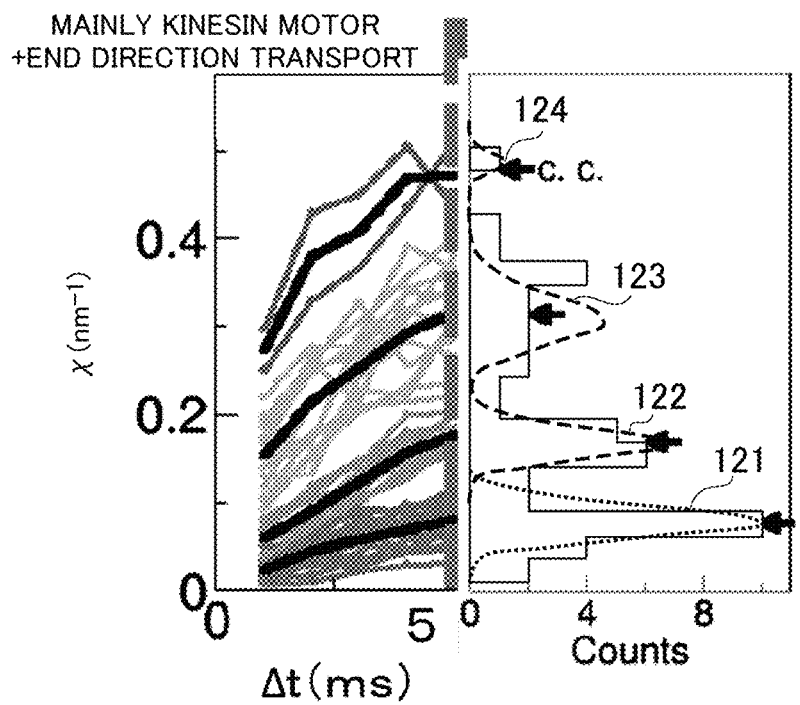
FIG. 17A is a diagram showing that a difference in the frequency distribution of the fluctuation value $\chi$ between when an endosome is transported by kinesin and when an endosome is transported by dynein is clear from measurement using the force measurement device 1 of the embodiment.
Figure 17B:
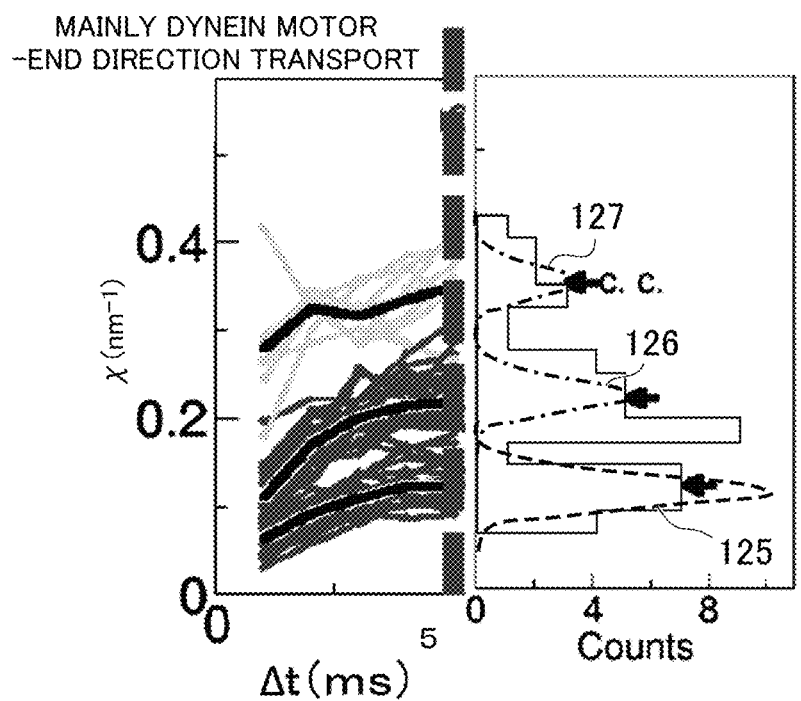
FIG. 17B is a diagram showing that a difference in the frequency distribution of the fluctuation value $\chi$ between when an endosome is transported by kinesin and when an endosome is transported by dynein is clear from measurement using the force measurement device 1 of the embodiment.

FIG. 17A and FIG. 17B are diagrams showing that a difference in the frequency distribution of the fluctuation value χ between when an endosome is transported by kinesin and when an endosome is transported by dynein is clear from measurement using the force measurement device 1 of the embodiment.

FIG. 17A is a diagram showing the distribution of χ when the endosome 201 is transported by the kinesin 202 shown in FIG. 16A. In FIG. 17A, for the fluctuation value χ, the distribution of data is classified into four clusters (clusters 121 to 124). Clustering is the result of clustering analysis.

FIG. 17B is a diagram showing the distribution of χ when the endosome 201 is transported by the dynein 203 shown in FIG. 16B. In FIG. 17B, for the fluctuation value χ, the distribution of data is classified into three clusters (clusters 125 to 127).

Comparing FIG. 17A and FIG. 17B, it shows that the frequency distribution of the fluctuation value χ differs between when the endosome 201 is transported from the cell center to the cell membrane, and when the endosome 201 is transported from the cell membrane to the cell center.

Modified Examples

Functional units of the force measurement device 1 and the fluctuation coefficient calculation device 2 need not necessarily be mounted in different housings but may be mounted in one housing.

Here, the second trajectory data acquisition unit 21 need not necessarily acquire time course data including constant speed movement data and stationary data based on observation data, but may acquire time course data acquired by the first trajectory data acquisition unit 11 and acquire time course data including constant speed movement data and stationary data among the acquired time course data.

Here, the time course data including constant speed movement data acquired by the first trajectory data acquisition unit 11 may be generated by a user based on observation data or may be generated by a device. In addition, the time course data including constant speed movement data and stationary data acquired by the second trajectory data acquisition unit 21 may be generated by a user based on observation data or may be generated by a device. The constant speed movement data used by the fluctuation value calculation unit 12 to calculate a fluctuation value may be selected manually by a user or selected by a device.

The constant speed movement data and stationary data used by the fluctuation coefficient calculation device 2 may be selected manually by a user or may be selected by a device. In addition, the cargo to be observed may be selected manually by a user or may be selected by a device.

Here, the image data group and observation data need not necessarily be 2D data but may be 3D or 1D data.

The force measurement device 1 and the fluctuation coefficient calculation device 2 in the above-described embodiments may be realized in a computer. In this case, a program for realizing this function is recorded in a computer readable recording medium, and a computer system is caused to read and execute the program recorded in the recording medium for realization. Here, "computer system" includes an OS and hardware such as peripheral devices. In addition, "computer readable recording medium" refers to a portable medium such as a flexible disk, a magneto-optical disc, a ROM, and a CD-ROM, and a storage device such as a hard disk built into a computer system. In addition, the "computer readable recording medium" may include a medium that dynamically maintains a program for a short time like a communication line when a program is transmitted via a network such as the Internet or a communication line such as a telephone line, and a medium that maintains a program for a certain time like a volatile memory in the computer system serving as a server or a client in that case. In addition, the program may be a program for realizing some of the above-described functions, a program that can be realized in combination with a program in which the above-described functions are already recorded in a computer system, or a program that is realized using a programmable logic device such as a field programmable gate array (FPGA).

In the above-described embodiments, the present invention is expressed as the force measurement device, but the present invention can also be expressed as a force measurement method. In this case, the force measurement method according to the present invention corresponding to the force measurement device in the embodiment can be expressed as a force measurement method including a first acquisition step in which, among data included in time course data indicating a movement trajectory of cargo acquired in a non-invasive manner, first data indicating a temporal change of a position of the cargo during a period in which the displacement of the cargo per unit time is substantially constant is acquired, a fluctuation value calculation step in which, based on a first probability distribution indicating a distribution of a probability that the amount of change at a predetermined position of the cargo per unit time is a predetermined amount, which is a probability distribution based on the first data, a fluctuation value proportional to a force applied to the cargo by motor proteins that transport the cargo is calculated, and a force calculation step in which the force is calculated based on the calculated fluctuation value.

In the force measurement method corresponding to the force measurement device in the above embodiment, the first acquisition step corresponds to an operation or process of the first trajectory data acquisition unit 11 in the embodiment, and the fluctuation value calculation step corresponds to an operation or process of the fluctuation value calculation unit 12 and the repetitive control unit 13 in the embodiment. In addition, the force calculation step corresponds to an operation or process of the force calculation unit 16 in the embodiment.

Here, the operation or process of the second trajectory data acquisition unit 21 in the embodiment is an example of the second acquisition step, and the operation or process of the fluctuation coefficient calculation unit 23 in the embodiment is an example of the fluctuation coefficient calculation step.

Here, the first trajectory data acquisition unit 11 is an example of a first acquisition unit. Here, the second trajectory data acquisition unit 21 is an example of a second acquisition unit. Here, constant speed movement data is an example of first data. Here, stationary data is an example of second data.

While the embodiments of the invention have been described above in detail with reference to the drawings, specific configurations are not limited to the embodiments, and include designs and the like without departing from the spirit of the invention.

REFERENCE SIGNS LIST

1 Force measurement device
2 Fluctuation coefficient calculation device
11 First trajectory data acquisition unit
12 Fluctuation value calculation unit
13 Repetitive control unit
14 Clustering unit
15 Fluctuation coefficient storage unit
16 Force calculation unit
21 Second trajectory data acquisition unit
22 Viscosity coefficient calculation unit
23 Fluctuation coefficient calculation unit
100 Force measurement system

The invention claimed is:

1. A force measurement method, comprising:
a first acquisition step in which, among data included in time course data indicating a movement trajectory of cargo acquired in a non-invasive manner, first data indicating a temporal change of a position of the cargo during a period in which the displacement of the cargo per unit time is substantially constant is acquired;
a fluctuation value calculation step in which, based on a first probability distribution indicating a distribution of a probability that the amount of change at a predetermined position of the cargo per unit time is a predetermined amount, which is a probability distribution based on the first data, a fluctuation value proportional to a force applied to the cargo by motor proteins that transport the cargo is calculated; and
a force calculation step in which the force is calculated based on the calculated fluctuation value.

2. The force measurement method according to claim 1, wherein, in the force calculation step, the force is calculated by performing clustering on the fluctuation value.

3. The force measurement method according to claim 1, further comprising:
a second acquisition step in which, among time course data indicating a movement trajectory of the cargo acquired in a non-invasive manner, time course data including the first data and second data indicating a temporal change of the position of the cargo during a period in which the position of the cargo is substantially the same position regardless of time is acquired; and
a fluctuation coefficient calculation step in which a fluctuation coefficient which is a conversion coefficient with respect to between the force and the fluctuation value is calculated based on the first and second data.

4. The force measurement method according to claim 3, wherein, in the fluctuation coefficient calculation step, a viscosity coefficient of a medium surrounding the cargo is calculated based on the second data.

5. The force measurement method according to claim 4, wherein, in the fluctuation coefficient calculation step, a speed at which the cargo moves is calculated based on the first data acquired in the second acquisition step.

6. The force measurement method according to claim 5, wherein, in the fluctuation coefficient calculation step, the fluctuation coefficient is calculated based on the viscosity coefficient and the speed.

7. The force measurement method according to claim 1, wherein, in the fluctuation value calculation step, $\chi$ is calculated according to a formula of $\chi = \ln[P1(\Delta X_1)/P1(-\Delta X_1)]\Delta X_1$ when the amount of change in the position is set as $\Delta X$, a probability that the value of $\Delta X$ during the unit time is $\Delta X_1$ is set as a first probability $P1(\Delta X_1)$, and the fluctuation value is set as $\chi$.

8. A force measurement device, comprising:
a first acquisition unit configured to acquire first data indicating a temporal change of a position of cargo during a period in which the displacement of the cargo per unit time is substantially constant among data included in time course data indicating a movement trajectory of the cargo acquired in a non-invasive manner;
a fluctuation value calculation unit configured to calculate, based on a first probability distribution indicating a distribution of a probability that the amount of change at a predetermined position of the cargo per unit time is a predetermined amount, which is a probability distribution based on the first data, a fluctuation value proportional to a force applied to the cargo by motor proteins that transport the cargo; and
a force calculation unit configured to calculate the force based on the calculated fluctuation value.

9. A non-transitory computer readable recording medium storing a program causing a computer to:
acquire first data indicating a temporal change of a position of cargo during a period in which the displacement of the cargo per unit time is substantially constant among data included in time course data indicating a movement trajectory of the cargo acquired in a non-invasive manner;
calculate, based on a first probability distribution indicating a distribution of a probability that the amount of change at a predetermined position of the cargo per unit time is a predetermined amount, which is a probability distribution based on the first data, a fluctuation value proportional to a force applied to the cargo by motor proteins that transport the cargo; and
calculate the force based on the calculated fluctuation value.

* * * * *

UNITED STATES PATENT AND TRADEMARK OFFICE
CERTIFICATE OF CORRECTION

PATENT NO. : 11,448,563 B2
APPLICATION NO. : 16/759040
DATED : September 20, 2022
INVENTOR(S) : Kumiko Hayashi et al.

It is certified that error appears in the above-identified patent and that said Letters Patent is hereby corrected as shown below:

In the Claims

At Column 20, Claim 7, Lines 19-20:
"calculated according to a formula of $\chi=\ln[P1(\Delta X_1)/P1(-\Delta X_1)]\Delta X_1$ when the amount of change in the position"

Should read:
"calculated according to a formula of $\chi=\ln[P1(\Delta X_1)/P1(-\Delta X_1)]/\Delta X_1$ when the amount of change in the position"

Signed and Sealed this
Twenty-eighth Day of February, 2023

Katherine Kelly Vidal
*Director of the United States Patent and Trademark Office*